(12) United States Patent
Paavola

(10) Patent No.: US 8,155,426 B2
(45) Date of Patent: Apr. 10, 2012

(54) INSPECTION OF WOOD SURFACE ROUGHNESS

(75) Inventor: Jyri Paavola, Tuusula (FI)

(73) Assignee: Oy Ekspansio Engineering Ltd., Kerava (FI)

( * ) Notice: Subject to any disclaimer, the term of this patent is extended or adjusted under 35 U.S.C. 154(b) by 1076 days.

(21) Appl. No.: 11/597,497

(22) PCT Filed: May 16, 2005

(86) PCT No.: PCT/FI2005/000221
§ 371 (c)(1),
(2), (4) Date: Dec. 31, 2007

(87) PCT Pub. No.: WO2005/116579
PCT Pub. Date: Dec. 8, 2005

(65) Prior Publication Data
US 2008/0239287 A1    Oct. 2, 2008

(30) Foreign Application Priority Data
May 27, 2004  (FI) ..................... 20040726

(51) Int. Cl.
*G06K 9/00* (2006.01)
*G01N 21/00* (2006.01)
*G01N 21/86* (2006.01)

(52) U.S. Cl. ............ 382/141; 382/108; 356/237.1; 250/559.25

(58) Field of Classification Search .............. 382/141, 382/100, 107, 108, 111, 148, 151, 152, 190, 382/216, 312; 356/391, 376, 371, 237, 394, 356/237.1, 402, 407; 358/101, 106, 107; 364/551.01; 209/580, 581, 582, 587; 348/92, 348/93, 370; 52/313, 784.1; 428/105; 250/559.04, 250/559.05, 559.07, 559.08, 559.1, 559.39, 250/559.4, 559.25, 226, 223 R
See application file for complete search history.

(56) References Cited

U.S. PATENT DOCUMENTS
4,290,698 A    9/1981    Milana
(Continued)

FOREIGN PATENT DOCUMENTS
| | | |
|---|---|---|
| CA | 1078489 | 5/1980 |
| DE | 3406375 | 8/1985 |
| EP | 0046058 | 2/1982 |
| EP | 0979995 | 2/2000 |
| EP | 1089106 | 4/2001 |

(Continued)

OTHER PUBLICATIONS

"A single chip multi-function sensor system for wood inspection;" Astrand E; Astrom A., Pattern Recognition, 1994, vol. 3—Conference C: Signal Processing, proceedings of the 12$^{th}$ IAPR International Conference; Oct. 9, 1994; p. 300-304.

*Primary Examiner* — Sheela Chawan
(74) *Attorney, Agent, or Firm* — Alfred A. Fressola; Ware, Fressola, Van Der Sluys & Adolphson LLP

(57) ABSTRACT

The invention relates to a method for optical inspection of the hirsuteness of a surface. The method comprises directing a light beam (B) to the surface (2) of a wooden piece (1) under study in a direction (D), which deviates from the normal to the surface. The surface is imaged with a camera (8) having an image plane (9) formed by several optoelectronic light-sensitive pixels by imaging at predetermined intervals the surface of the wooden piece moving relative to the camera, each image being in the form of electronic image data. The image data of two consecutive electronic images are subtracted from each other, yielding a set of pixel-related difference data describing the wooden surface under study, and the difference data are used for stating varitions in the surface roughness of the surface under study.

11 Claims, 3 Drawing Sheets

U.S. PATENT DOCUMENTS

| | | | |
|---|---|---|---|
| 4,878,114 A | 10/1989 | Huynh et al. | |
| 5,229,835 A | 7/1993 | Reinsch | |
| 5,644,392 A * | 7/1997 | Soest et al. | 356/237.1 |
| 5,960,104 A * | 9/1999 | Conners et al. | 382/141 |
| 6,122,065 A * | 9/2000 | Gauthier | 356/394 |
| 6,614,041 B1 | 9/2003 | Lappalainen et al. | |
| 6,624,883 B1 * | 9/2003 | Zhou et al. | 356/237.1 |
| 7,406,190 B2 * | 7/2008 | Carman et al. | 382/141 |

FOREIGN PATENT DOCUMENTS

| | | |
|---|---|---|
| EP | 1355148 | 10/2003 |
| FI | 763517 | 6/1978 |
| JP | 61259112 | 11/1986 |
| JP | 08292158 | 11/1996 |
| PL | 271737 | 1/1990 |
| WO | WO 02075295 | 9/2002 |

\* cited by examiner

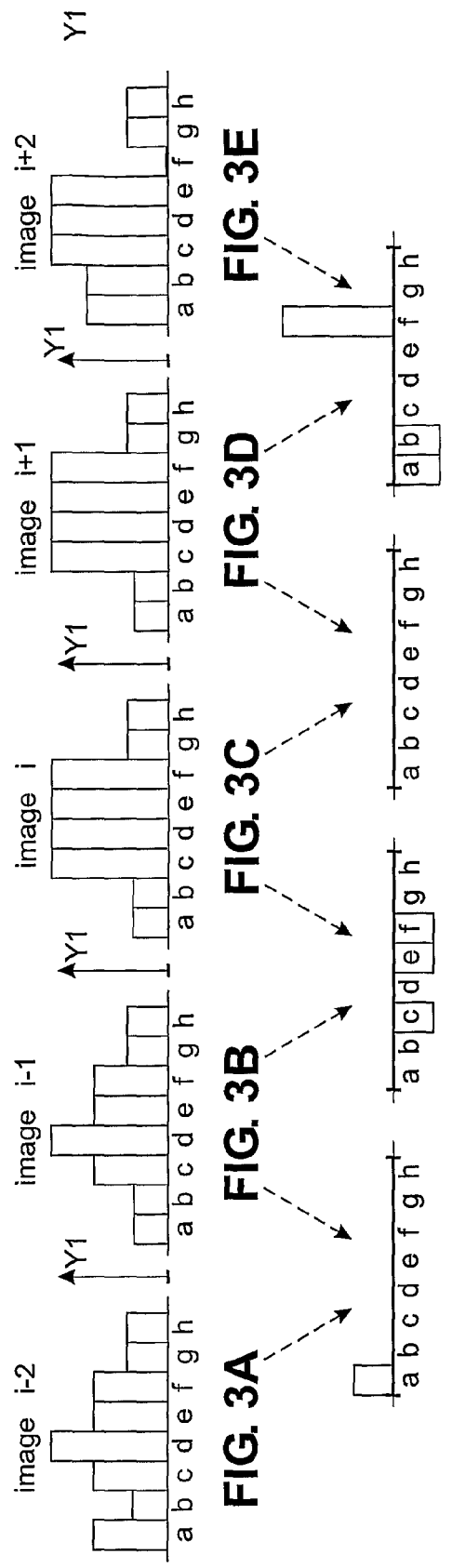
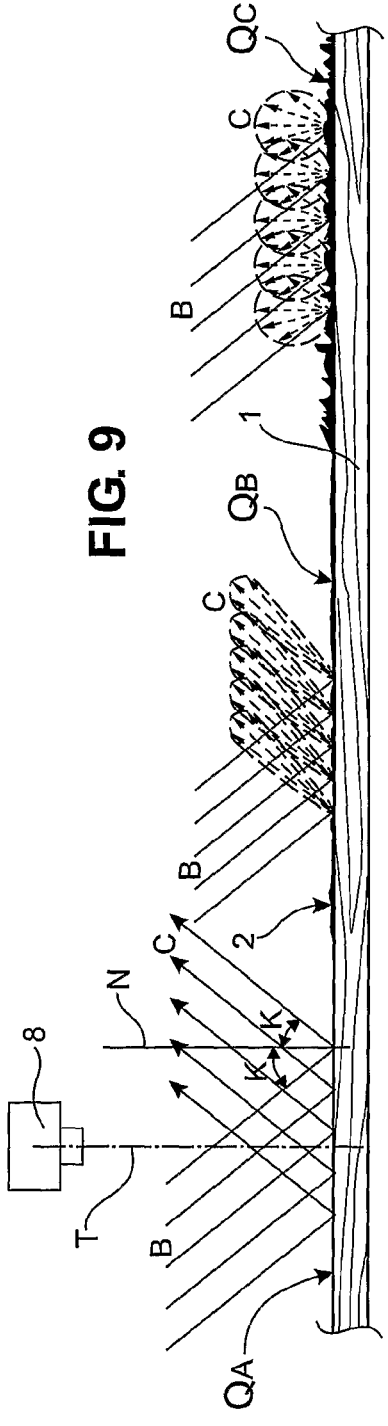

INSPECTION OF WOOD SURFACE ROUGHNESS

CROSS REFERENCE TO RELATED APPLICATIONS

This application is for entry into the U.S. national phase under §371 for International Application No. PCT/FI05/000221 having an international filing date of May 16, 2005, and from which priority is claimed under all applicable sections of Title 35 of the United States Code including, but not limited to, Sections 120, 363 and 365(c) and which in turn claims priority under Section 119 to Finnish Patent Application No. 20040726 which was filed on May 27, 2004.

TECHNICAL FIELD

The invention relates to a method for optical inspection of surface roughness, in which a light beam is directed to the surface to be inspected; said surface and the light beam are shifted relative to each other; the light reflected from said surface is received with an optoelectronic detector; and values corresponding to the surface roughness are calculated on the electric signal produced by the detector.

BACKGROUND OF THE INVENTION

Measurement of surface roughness in general is difficult, and measurement of the roughness of smooth surfaces and especially of wooden surfaces is both awkward and inaccurate. The problem arising in roughness measurement of wooden surfaces is caused among other things by the fact that, unlike any other material, the roughness of wood consists partly of surface hirsuteness generated by loose wooden fibres, U.S. Pat. No. 6,122,065 describes an arrangement in which the topology of an object, such as the surface of a piece of wood, is inspected using a camera and monochromatic laser light, and the surface profile is determined utilising the triangulation based derivation method. This arrangement aims at localisation of cavities, wane and other missing material. In addition, this reference combined with the procedure mentioned above allows for colour analysis of the wooden surface using either two LEDs of different colours, which consequently emit light on two wavelengths, or wideband light together with spectroanalysis. This part of the arrangement searches other issues than shape deficiencies. The procedure of the reference is not capable of measuring surface roughness in the form of hirsuteness, but only major shape deficiencies, as it appears from the reference itself. Patent specifications U.S. Pat. Nos. 4,290,698, 4,878,114, 5,229,835 and CA-1078489 describe similar methods for measuring surface roughness by directing a narrow light beam to the surface to be inspected, by receiving the light reflected by said surface by means of an optoelectronic detector moved in parallel with the surface, and by calculating values corresponding to the surface roughness on the electric signal obtained. In all of these references, surface undulation is regarded as surface roughness. Surface undulation results in the grazing angle of the reflected beam relative to the mean normal to the surface varying in accordance of the current angle of inclination of the surface, and then the amount of light reflected at a given angle also varies and is measurable. These methods are hence statistic methods as well, in other words, they calculate the standard deviation, root mean squares or the like, and the quantity of microundulation of the surface is derived from these. FR patent specification 2 710 405 depicts a method for quantitative determination of the roughness of a wooden surface by using measurement of the frictional energy of a rotating feeler. This is hence a mechanical probe, which is inappropriate for comprehensive inspection of large amounts of timber, and especially for inspection of surface roughness distributions with respect to all the timber passing through a production line.

SUMMARY OF THE INVENTION

The invention has the purpose of achieving an arrangement and a method allowing inspection of one or more surfaces of a piece of timber at a high speed, completely if necessary, in order to determine whether these surfaces include zones whose surface roughness, i.e. hirsuteness in this case of wooden surfaces, has unacceptable deviation. The invention has the second purpose of achieving an arrangement and a method providing relevant information about the roughness, i.e. hirsuteness of a wooden surface, independently of the colour or darkness or grain or grain darkness variations or grain direction of the wood species. Thus, for instance, the wood grain, i.e. darkness and colour variation of the wooden surface, should not be indicative of variations in "surface roughness" when the real hirsuteness remains quite constant over the surface. Also the direction into which the probe is moved relative to the wood grain direction should not yield different "surface roughness values", given that the hirsuteness of a wooden surface is always oriented to some extent, in cases where the real hirsuteness is quite identical. In addition, the arrangement and the method should be suitable for inspecting each location even of large surfaces, in other words, they should allow for inspection of potential locations with different surface roughness or hirsuteness of a given surface.

The problems above are eliminated and the purposes defined above are achieved with the method of the invention. This method is thus a method for optical inspection of surface roughness, comprising:
  directing an unfocussed light beam to a surface of a piece of wood to be inspected in a direction, which deviates from the normal to said surface;
  shifting said surface and light beam relative to each other;
  receiving light reflected from said surface with an optoelectronic detector;
  calculating values corresponding to the surface roughness on the electronic signal produced by the detector, wherein said body is a piece of wood and said surface roughness is hirsuteness of the wooden surface,
  using as the optoelectronic detector a camera having an image plane formed of several light-sensitive optoelectronic pixels;
  taking at predetermined intervals images (i−n . . . i+n) of said surface of the piece of wood moving relative to the camera, each image having the form of electronic image data;
  subtracting the image data of two consecutive electronic images from each other, yielding a set of pixel-related difference data ((i−n)−(i−(n−1))) . . . (i+(n−1))−(i+n)), which describes the wooden surface under study; and
  using the difference data for stating variations in the surface hirsuteness of the surface under study.

The chief advantage of the invention is that it enables inspection of adequate planing of e.g. planed timber and thus of the surface quality of the product, without touching the timber, at a high speed and automatically. This is achieved by using an optical method. The invention also has the essential advantage of allowing elimination of the effect of the wood grain, i.e. of the darkness variation of the wooden surface, although the invention relates to an optical method based on reflectivity. The result of the inspection is correct, i.e. the surface roughness data comply with the real roughness, even though the light reflectivity varies in accordance with the overall and local colour or darkness of the wood.

BRIEF DESCRIPTION OF THE DRAWINGS

The invention is explained in greater detail below with reference to the accompanying drawings.

FIGS. 3A-3E are simplified and principal views of a number of linear images, with consecutive images taken at small intervals of the surface of a moving object and consisting of pixels having values stored in electronic form and imaging the surface of the object.

FIGS. 4A-4D are simplified and principal views of a number of linear images generated by subtracting the pixel-related electronic values of two consecutive images, i.e. of two images 3A-3E, from each other.

FIG. 9 shows how the type of reflectivity of oblique incident light on a wooden surface, especially of unfocused light, varies depending on the nature of different points of this planar wooden surface, i.e. not hirsute, moderately i.e. slightly hirsute, or very coarse, i.e. strongly hirsute points.

DETAILED DESCRIPTION

Figure 1A:
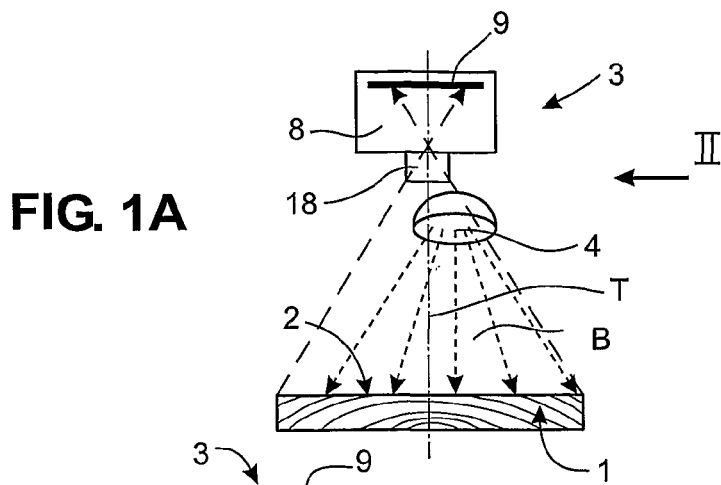
FIGS. 1A and 1B illustrate an arrangement for implementing the method of the invention, viewed in the direction of movement of a moving object, corresponding to direction I in FIG. 2.
Figure 8:
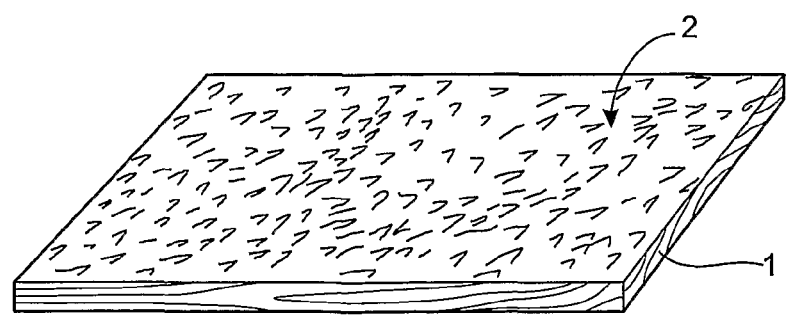
FIG. 8 is a schematic view of the typically hirsute surface structure of a timber piece in axonometric projection.

FIGS. 1A. 1B and 2 illustrate an apparatus by means of which the method of the invention for optical inspection of surface roughness can be implemented. The object whose surface 2 is inspected by the procedure of the invention is a piece of wood 1, such as a board, a plank, a plate or any other body having at least one exact surface shape and consisting principally of wood. In this context, piece of wood 1 consequently implies not only "massive" wood, but also veneer, multi-layered wood, or even a laminate, provided that the inspected surface is made of wood or may have a surface structure corresponding to a wooden surface. The surface structure of the piece of wood 1 may vary from very smooth, such as a high-quality planed surface or a polished surface having a very fine-grained polished surface, to a very rough and hirsute surface, such as a sawn, sand-blasted, water-sprayed or splintered surface. Greater or smaller hirsuteness of the surface of a piece of wood, which is due to the fibre structure, is characteristic especially of the roughness of a wooden surface, and such a surface 2 is illustrated in FIG. 8. The invention investigates the respective location of the wooden surface in the variation range rough i.e. hirsute÷smooth, i.e. its roughness, i.e. hirsuteness. The piece of wood may also be surface-treated, and then the method of the invention also enables examination of adequate surface treatment, among other things. Surface treatment of wood, such as painting or varnishing, accentuates grains in the wooden surface, i.e. precisely roughness and hirsuteness, the method of the invention being well adapted to this determination. The concept "roughness" used in connection with the invention in this description implies explicitly a surface of "hirsute" type as described above.

Firstly, the apparatus comprises a light source 4, more specifically either one single light source or a light source array consisting of several components, emitting an unfocused light beam B consisting of incoherent radiation to the surface 2 of the piece under study. The invention preferably uses one single light source 4, which may, of course, comprise a plurality of radiation sources, such as incandescent bulbs, arc tubes or LEDs next to each other. If several light sources are used, they should nevertheless all be located at least within the same semi-space and emit light into the direction explained below. However, it is most advantageous to provide a point-like light source 4 or a light source as close to point-like as possible, in other words, with its properties approaching those of a point light source. This arrangement yields the best quality of the image taken of the surface 2 of the piece of wood 1 under study. A horizontally placed linear light source may also be usable. The light source 4 may emit radiation on visible wavelengths and/or in the near infrared range and/or near ultraviolet range, and the light source is typically a broadband light source, i.e. such that emits on a plurality of different wavelengths, but a narrow emission band or even a monochromatic emission band can also be applied. In any case, the light beam B from the light source is directed to the surface 2 to be inspected in direction D, which deviates from the normal N to said surface. In accordance with the invention, said direction D of the light beam, more precisely the mean direction D, is at an angle K to the normal N to the surface under study, with the angle K in the range 30°-6°. A light beam having a mean direction forms one single light beam even though the light source itself would consist of a plurality of radiating elements. The angle of incidence K of the light beam should also be selected such that the beams that are mirror reflected from the surface of the body, this situation being a theoretical one, do not reach the camera, but pass by its imaging optics 17, 18. The light beam B should also have a width such that it illuminates the entire image area $A_K$ of which the consecutive images are taken. In the case of a piece of wood, for instance, an imaging width $W_K$ corresponding to the entire width W of the piece in a direction perpendicular to the direction of movement M is illuminated, and over a length $L_K$ in the direction of movement M of the piece to the extent corresponding to the image area stored by the camera in this direction. The image area $A_K$ stored by camera 8, in this case a line camera, has been marked in FIG. 5, in a situation where the imaging width is at least equal to the width of the piece of wood $W_K \geq W$, and the illuminated area $A_V$, which is slightly larger than the image area $A_K$. One should try to keep the amount of actual diffused light, i.e. of light incident on the surface 2 from all directions, at a minimum, because it reduces the contrast and thus the resolution. The light beam B consists preferably of directional light alone, which preferably is unfocused and incoherent.

FIG. 9 shows what is currently believed to happen on the inspected surface 2 when the light beam B, actually a large set of light beams, hit at oblique incidence angle K areas $Q_A$, $Q_B$, $Q_C$ having surface roughness, i.e. hirsuteness of different types. On the one hand, the type of reflection of the incident light on the wooden surface, especially of unfocused light, changes under varied diffusion, and on the other hand, under varied shade formation caused by hirsuteness. In the example of FIG. 9, all the areas $Q_A$, $Q_B$, $Q_C$ of different types are in the same plane. When the first area $Q_A$ of this planar wooden surface 2 is completely free of hirsuteness, i.e. completely smooth, the incident beam B is mirror reflected, the angle of departure K of the departing light beam C being the same as the angle of incidence. When the third area $Q_C$ of this planar wooden surface is totally rough, i.e. totally hirsute, the incident beam is reflected from the Lambert surface, i.e. is diffusely reflected from the surface 2 into all directions as beams C in a manner unaffected by the incidence direction, in other words it follows Lambert's cosinus law. When the second area QB of this planar wooden surface is slightly rough, i.e. slightly hirsute, the incident light beam B is reflected with a portion at the departure angle K of the source or at angles close to the departure angle K, and a minor portion into directions deviating considerably from the departure angle. In the practice, however, the real wooden surfaces 2 are at a value between the extreme values, i.e. of a type similar to that of the second surface $Q_B$, with a reflection type approaching either more the first surface type $Q_A$ or the third surface type $Q_C$. A different type of reflection generates a different quantity of light in a perpendicular direction N, corresponding to the direction of the optical axis T of the camera array, away from the surface 2, and this is the very radiation portion examined by means of the arrangement of the invention.

Figure 1B:
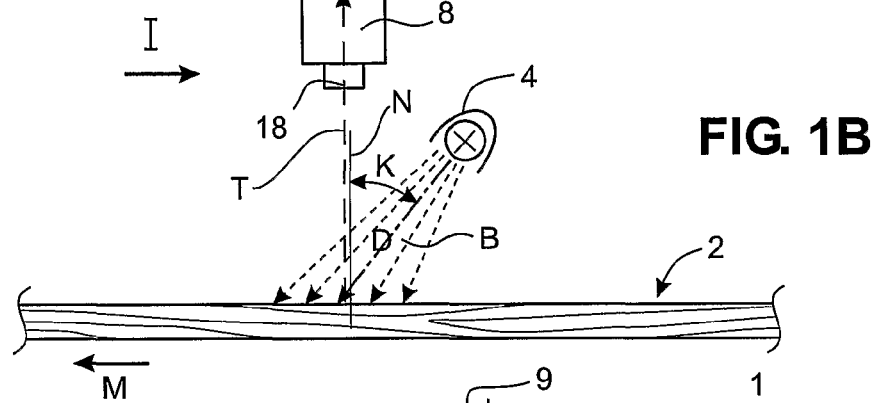
Figure 2:
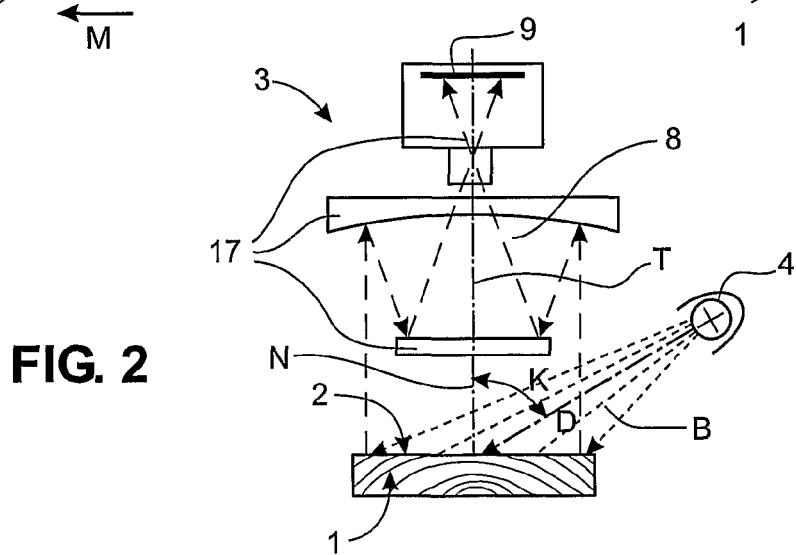
FIG. 2 illustrates the arrangement of FIG. 1 for implementing the method of the invention, viewed in a direction perpendicular to the direction of movement of the object, corresponding to direction II in FIG. 1.

The apparatus also comprises a camera 8 acting as an optoelectronic detector 3, which comprises an image plane 9 formed of a plurality of light-sensitive optoelectronic pixels. The camera 8 may consist of a camera equipped with conventional imaging optics 18—as in FIGS. 1A and 1B—thus imaging an image in the central perspective of the surface of the piece of wood, or more advantageously the camera 8 consists of a camera equipped with telecentric imaging optics 17—e.g. as the one illustrated in FIG. 2—in other words, a telecentric camera. The camera 8 may further be of the type in which the image plane is formed of two dimensions, i.e. comprising several pixels in two mutually perpendicular directions, or more advantageously a line camera, whose image plane consists of one single row of light-sensitive pixels. The image plane 9 of the camera 8 has a number of pixels such and the imaging ratio of the camera has been arranged such that the entire width W of a moving piece of wood is imaged on the image plane 9. This can be done in a commonly known manner by selecting both the size of the image plane 9 and the focal length of the objective and by setting the imaging distance, and hence this matter is not explained more in detail here. If desired, it is naturally possible to image only a portion of say, the width of a board, the imaging width being then smaller than the width of the piece of wood, i.e. $W_K$<W, but in any case, imaging relates to a large set of pixels and not in any case only to one single pixel. The optical axis T of the camera 8 and its imaging optics 17 or 18 is preferably perpendicular to the surface 2 to be examined on the piece 1, so that small deviations are naturally permissible.

The light source 4 and the camera 8 form a stationary apparatus. For the method of the invention, the surface 2 to be examined on the piece of wood is displaced, naturally by shifting the piece of wood 1 itself into direction M relative to the stationary light beam B and the camera 8. The actuating mechanism of the piece of wood 1 does not relate to the invention, and it can be of any type suitable for the purpose, and consequently, it is not explained in further detail here. The surface 2 of the piece of wood reflects a portion of the incident light away from the surface. This light reflected from the surface 2 is received by the camera 8, so that the light-sensitive optoelectronic pixels forming its image plane 9 generate an electronic signal, or in this case, pixel-related electronic image data. The image data allow calculation of values corresponding to the surface roughness or to variations of surface roughness in the manner explained more in detail below.

Figure 5:
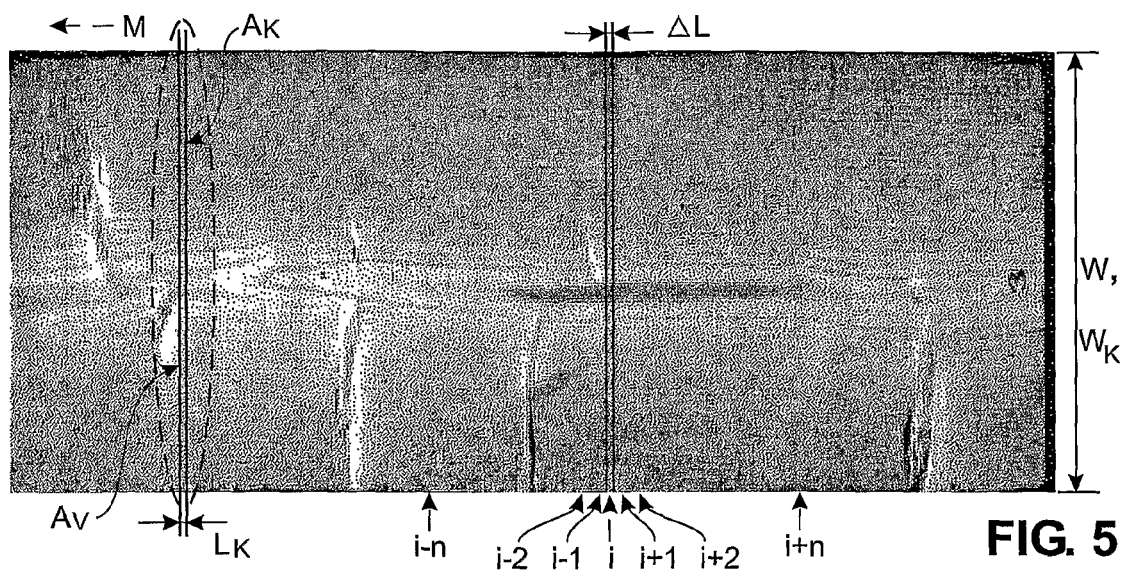
FIG. 5 shows a typical surface of a timber piece that has been formed by associating a large set of electronic linear images taken in succession adjacent each other, the result also corresponding to a conventional photograph.
Figure 6:
FIGS. 6 and 7 show the surface of the timber piece of FIG. 5 in the images of the invention, i.e. the image generated from the differences of consecutive linear images by placing them adjacent each other, these two images differing only by their inverse darkness values.
Figure 7:
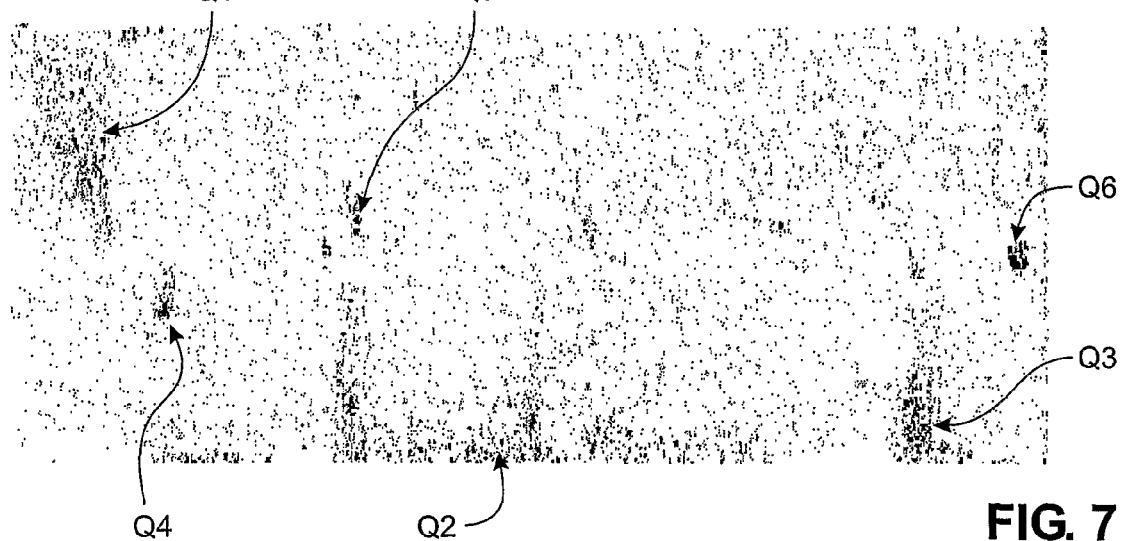

The camera is used to take images at predetermined intervals ΔL of said surface 2 of the piece of wood moving relative to the camera, the surface being illuminated with directional and focused light, as explained above. Consecutive images having an image area $A_K$ are taken of the surface 2 of the piece of wood while the piece of wood moves in front of the camera 8 and the associated light source 4 located on one of its sides, the camera taking a series of images i–n . . . i–2, i–1, i, i+1, i+2, i+3 . . . i+n, each of the images being in the form of electronic image data. The distances between these consecutive images i–n . . . i–2, i-1, i, i+1, i+2, i+3 . . . i+n on the surface of the piece of wood are spaced by the time and length interval ΔL mentioned above. The predetermined imaging intervals ΔL in the direction of movement of the piece of wood are less than 1.5 mm or preferably at the most 0.5 mm. FIGS. 3A-3E illustrate extremely simple examples of five consecutive images, e.g. images i–2, i–1, i, i+1, i+2, i+3 (image i–2, image i–1, image i, image i+1, image i+2), each consisting of eight pixels a, b, c, d, e, f, g, h. Each pixel has an electronic signal value proportional to the light intensity received by the camera 8, illustrated in the figures by the height Y1 of the pixel. With a plurality of such images disposed in parallel on the correct scale relative to the distance ΔL, a conventional photograph in the central perspective or a telecentric photograph is generated. FIG. 5 illustrates an example of this, showing the surface of a piece of wood including grains and knots. In accordance with the invention, the image data of two respective consecutive electronic images are subtracted from each other, yielding a set of pixel-related difference data, which illustrates the wood surface under study. FIGS. 4A-4D show the pixel-related difference data of the image data in FIGS. 3A-3E, i.e. the image data of FIG. 3A minus the image data of FIG. 3B, the image data of FIG. 3B minus the image data of FIG. 3C, etc. In other words, FIGS. 4A-4D show the following difference data (i–2)-(i–1) in FIG. 4A, (i–1)-(i) in FIG. 4B, (i)-(i+1) in FIG. 4C and (i+1)-(i+2) in FIG. 4D as defined by means of the original images. Generally defined, the difference data are a data set in the range (i–n)-(i–(n–1)) . . . (i+(n–1))-(i+n). These difference data are used in accordance with the invention for stating variations in the surface roughness of the inspected surface. FIGS. 6 and 7 show difference data of image data obtained on the surface of FIG. 5. It can be clearly seen that the surface grains and knots of the piece of wood have disappeared as intended, and an image remains whose darkness variations illustrate the surface roughness. In FIG. 6, the black areas represent a very smooth surface and the white points or areas represent a very rough surface, in FIG. 7, in turn, the white areas represent a very smooth surface and the black or dark points or areas a very rough or hirsute surface. The grey points or areas represent surface roughness located between the extreme values. Such images showing the surface of a piece of wood can be referred to as difference data images. One should understand that such images based on grey scale or surface darkness, i.e. the calculated density of hypothetically visible images, are but one among several manners of presenting the difference data. Thus, for instance, it is not at all necessary to display them as visible images at any stage, but the results of the calculations can be described or presented in other ways as well. Using a computer, for instance, one can calculate the distribution or distributions of pixel-related difference data describing extremely smooth and very coarse surface roughness and surface roughness values between these, using e.g. an appropriate statistical method for further operations, as explained below.

For the sake of illustration, this text goes on referring to images and image data, even if no concrete images visible to humans were used at all, since the data obtained are analogue with visual image data and the obtained data could, if desired, be consistently displayed with visible images. The method of the invention also defines in advance the threshold value or values of the surface darkness, i.e. the grey value of the grey scale, experimentally, for instance. This surface darkness or grey value may be the same as the commonly known optical density, $OD = Log_{10} (I_0/I)$, but may be values indicated on any other scale. Surface darkness values corresponding to the difference data explained above and illustrated in FIGS. 4A-4D and 6 and 7, respectively, can be determined 1} by imaging a given surface 2 and by generating a difference data image of this, 2} by examining this surface 2 with other methods and 3} by determining one or more threshold values for the darkness value of the pixel of the difference data image, these values corresponding to one or more specific flaw levels in the piece of wood 1 forming the product. Thus, for instance, regarding the embodiment of FIG. 6, it can be stated that, when the value of the pixel-related electronic signal describing darkness exceeds a first millivolt value, the product is either rejected or needs to be corrected, i.e. retreated. Several threshold values signify that stability degrees have been defined for surface roughness flaws, e.g. a relatively large flaw equalling a second millivolt value causes rejection and a smaller flaw equalling a third millivolt value (second millivolt value)>(third millivolt value) causes classification in a lower quality class or in any desired operation range. During the subsequent production of pieces of wood 1, the values of difference data are compared with this or these predetermined threshold values of surface darkness, and higher/lower values are examined in order to determine variations in the surface roughness of the inspected surface. As it appears from the explanation above, while processing the image data of the object or difference image data, it is not necessary to generate a visible image, but the roughness of the wooden surface 2 under study can be inferred merely by comparing the values of electronic signals. As can be seen in FIGS. 6 and 7, the inference is the same on principle, only the direction is inverse if the image data and the difference image data, i.e. the corresponding electronic signals, are inverted in a known manner.

It is understood that the darkness value of an individual pixel as such does not usually have a great impact when the values of difference data are compared pixel by pixel with a predetermined threshold value of the surface darkness, by contrast, usually only larger areas whose surface darkness values differ from the desired or planned darkness have a real significance. In that case, the number or proportion of pixels above/under the threshold value of the surface darkness is calculated on all the pixels included in the set of difference data describing this particular wood surface, and then the local darkness values of these above/under pixels, i.e. the darkness distributions per surface area of the wood are calculated. Thus, for instance, FIG. 7 shows three distinct and large concentration areas Q1, Q2, Q3, in which the surface roughness, i.e. surface hirsuteness is above a specific value, and three distinct but small concentration areas Q4, Q5, Q6, where the surface roughness, i.e. surface hirsuteness is above a specific value. According to the requirements posed on the product in each case, one can set predetermined limit values with the relationship⇒the density or number of pixels above the threshold value of surface darkness is greater than the predetermined density or number in an area of a specific size, or in the inverse case above⇒the density or number of pixels above the threshold value of the surface darkness is greater than the predetermined density or number in an area of a specific size. In this case, the piece of wood under study is subjected to predetermined actions—such as correction or rejection—on the basis of variations in surface roughness, i.e. surface hirsuteness, and naturally other potential measures—such as acceptance or classification in a higher quality class—when the situation is inverse, i.e. the density or number of pixels under the threshold value of the surface darkness is high. In this case as well, the predetermined density or densities or number(s) can be set on the basis of tests conducted in advance.

While there have been shown and described and pointed out fundamental novel features of the invention as applied to preferred embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A method for optical inspection of surface roughness, comprising:

directing an unfocussed light beam (B) to a surface (2) of a piece of wood to be inspected in a direction (D), which deviates from the normal to said surface;

shifting said surface and light beam relative to each other;

receiving light (R) reflected from said surface with an optoelectronic detector (3);

calculating values corresponding to the surface roughness on the electronic signal produced by the detector, wherein said surface roughness is hirsuteness of the wooden surface, using as the optoelectronic detector a camera (8) having an image plane (9) formed of several light-sensitive optoelectronic pixels;

taking at predetermined intervals images (i−n ... i+n) of said surface (2) of the piece of wood moving relative to the camera (8), each image having the form of electronic image data;

subtracting the image data of two consecutive electronic images from each other, yielding a set of pixel-related difference data ((i−n)−(i−(n−1)) ... (i+(n−))−(i+n)), which describes the wooden surface under study; and using the difference data for stating variations in the surface hirsuteness of the surface under study.

2. The inspection method as defined in claim 1, comprising:
   comparing the values of the difference data with one or more predetermined threshold values of surface darkness; and
   using values above/under the threshold values of the surface darkness in order to state variations in the surface hirsuteness of the surface under study.

3. The inspection method as defined in claim 2, wherein said one or more threshold values of the surface darkness are set on the basis of tests that have been conducted in advance.

4. The inspection method as defined in claim 1, comprising:
   comparing by pixels the values of the difference data with a predetermined threshold value of the surface darkness;
   calculating the proportion or number of pixels above/under the threshold value of the surface darkness in all the pixels included in the set of difference data describing the wooden surface under study;
   calculating the density or density distribution per wooden surface unit of pixels having said above/under values; and
   if the density of pixels above/under the threshold value of the surface darkness is above/under the predetermined density, subjecting this particular piece of wood to predetermined actions on the basis of variations in the surface hirsuteness.

5. The inspection method as defined in claim 4, wherein said predetermined density is set on the basis of tests that have been conducted in advance.

6. The inspection method as defined in claim 1, wherein said predetermined imaging intervals ($\Delta L$) in the direction of movement of the piece of wood are under 1.5 mm, or 0.5 mm at the most.

7. The inspection method as defined in claim 1 wherein the image plane (9) of said camera has a number of pixels and the imaging ratio of the camera has been disposed so that the entire width (W) of a moving piece of wood is imaged on the image plane.

8. The inspection method as defined in claim 1, wherein a telecentric line camera is used as said camera (8).

9. The inspection method as defined in claim 1, wherein said unfocused light beam (B) consists of incoherent radiation, the plurality of wavelengths included in the radiation being between near-infrared—near-ultraviolet.

10. The inspection method as defined in claim 1, wherein said direction (D) of the light beam is at an angle (K) in the range 30°-60° to the normal to the surface under study.

11. The inspection method as defined in claim 1, wherein light (R) reflected from the wooden surface (2) is received in a direction (T) perpendicular to said surface.

* * * * *